United States Patent
Chheda et al.

(10) Patent No.: US 10,562,874 B2
(45) Date of Patent: Feb. 18, 2020

(54) PROCESS FOR THE RECOVERY OF FURFURAL

(71) Applicant: SHELL OIL COMPANY, Houston, TX (US)

(72) Inventors: Juben Nemchand Chheda, Houston, TX (US); Charu Ehrenreich-Gureja, Amsterdam (NL); Jean Paul Andre Marie Joseph Ghislain Lange, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 16/346,361

(22) PCT Filed: Oct. 30, 2017

(86) PCT No.: PCT/US2017/058936
§ 371 (c)(1),
(2) Date: Apr. 30, 2019

(87) PCT Pub. No.: WO2018/085174
PCT Pub. Date: May 11, 2018

(65) Prior Publication Data
US 2019/0270716 A1    Sep. 5, 2019

Related U.S. Application Data

(60) Provisional application No. 62/415,528, filed on Nov. 1, 2016.

(51) Int. Cl.
*C07D 307/02* (2006.01)
*C07D 307/48* (2006.01)
(Continued)

(52) U.S. Cl.
CPC .......... *C07D 307/48* (2013.01); *B01D 3/143* (2013.01); *B01D 3/36* (2013.01); *C07D 307/50* (2013.01)

(58) Field of Classification Search
CPC ......... C07D 307/48; B01D 3/143; B01D 3/36
(Continued)

(56) References Cited

U.S. PATENT DOCUMENTS 2,078,241 A  4/1937 Fulmer et al.
2,536,732 A  1/1951 Dunlop
(Continued)

FOREIGN PATENT DOCUMENTS

EP  1727890 A1  12/2006
EP  1863901 A1  12/2007
(Continued)

OTHER PUBLICATIONS

International Search Report and Written Opinion received for PCT Patent Application No. PCT/US2017/058936, dated Feb. 7, 2018, 9 pages.
(Continued)

*Primary Examiner* — Taylor V Oh

(57) ABSTRACT

A process for the extraction of furfural from a composition comprising furfural, water, at least one organic acid and an oxygenate solvent with a boiling point higher than that of furfural. The process includes: (a) subjecting the composition to a first liquid-liquid separation step to provide: (i) an organic phase; (b) subjecting the organic phase of step (a) to a first distillation step to provide: (i) a first top stream; (c) subjecting the first top stream of step (b) to a second liquid-liquid separation step to provide: (i) a second top stream; and (d) subjecting the second top stream of step (c) to a second distillation step to provide: (i) a third top stream
(Continued)

comprising a furfural-water azeotrope, and (ii) a third bottom stream comprising furfural.

7 Claims, 1 Drawing Sheet

(51) Int. Cl.
  *B01D 3/14* (2006.01)
  *B01D 3/36* (2006.01)
  *C07D 307/50* (2006.01)

(58) Field of Classification Search
  USPC .......................................................... 549/483
  See application file for complete search history.

(56) References Cited

U.S. PATENT DOCUMENTS

| | | | |
|---|---|---|---|
| 3,549,319 | A | 12/1970 | Wilson et al. |
| 4,409,032 | A | 10/1983 | Paszner et al. |
| 4,461,648 | A | 7/1984 | Foody |
| 4,533,743 | A | 8/1985 | Medeiros et al. |
| 5,536,325 | A | 7/1996 | Brink |
| 5,789,210 | A | 8/1998 | Ho et al. |
| 5,820,687 | A | 10/1998 | Farone et al. |
| 6,475,768 | B1 | 11/2002 | Otero et al. |
| 7,741,084 | B2 | 6/2010 | Viitanen et al. |
| 7,741,119 | B2 | 6/2010 | Viitanen et al. |
| 7,781,191 | B2 | 8/2010 | Dunson, Jr. et al. |
| 8,168,807 | B2 | 5/2012 | Wabnitz et al. |
| 8,466,242 | B2 | 6/2013 | Geremia et al. |
| 2003/0162271 | A1 | 8/2003 | Zhang et al. |
| 2009/0061490 | A1 | 3/2009 | Edwards et al. |
| 2010/0019191 | A1 | 1/2010 | Hoffer et al. |
| 2010/0312028 | A1 | 12/2010 | Olson et al. |
| 2012/0107887 | A1 | 5/2012 | Chheda et al. |
| 2012/0122152 | A1 | 5/2012 | Blackbourn et al. |
| 2012/0157697 | A1 | 6/2012 | Burket et al. |
| 2012/0302765 | A1 | 11/2012 | Dumesic et al. |
| 2013/0295629 | A1 | 11/2013 | Weider et al. |
| 2014/0018555 | A1 | 1/2014 | De Vries et al. |
| 2014/0107355 | A1 | 4/2014 | Dumesic et al. |

FOREIGN PATENT DOCUMENTS

| | | |
|---|---|---|
| RU | 1365674 A1 | 7/1996 |
| WO | 9742307 A1 | 11/1997 |
| WO | 2007009463 A2 | 1/2007 |
| WO | 2007028811 A1 | 3/2007 |
| WO | 2007136762 A2 | 11/2007 |
| WO | 2008119082 A2 | 10/2008 |
| WO | 2009109631 A1 | 9/2009 |
| WO | 2009130386 A1 | 10/2009 |
| WO | 2011161141 A1 | 12/2011 |
| WO | 2012027279 A1 | 3/2012 |
| WO | 2012041990 A1 | 4/2012 |
| WO | 2014105289 A1 | 7/2014 |
| WO | 2016025678 A1 | 2/2016 |
| WO | 2016025679 A1 | 2/2016 |

OTHER PUBLICATIONS

International Search Report and Written Opinion received for PCT Patent Application No. PCT/US2015/044994, dated Nov. 2, 2015, 8 pages.
International Search Report and Written Opinion received for PCT Patent Application No. PCT/US2015/044990, dated Nov. 2, 2015, 7 pages.
International Search Report and Written Opinion received for PCT Patent Application No. PCT/US2017/058942, dated Jan. 19, 2018, 9 pages.
International Search Report and Written Opinion received for PCT Patent Application No. PCT/US2017/058939, dated Dec. 14, 2017, 8 pages.
International Search Report and Written Opinion received for PCT Patent Application No. PCT/US2017/058951, dated Jan. 2, 2018, 8 pages.
Brown et al., "Fast Pyrolysis and Bio-Oil Upgrading", Biomass-to-Diesel Workshop; Pacific Northwest National Laboratory, Sep. 5-6, 2006.
Zeitsch, "The Chemistry and Technology of Furfural and its Many By-Products", Sugar Series, vol. 13, Feb. 1, 2000, pp. 48-51 and 303-306.
Galbe et al., "A Review of the Production of Ethanol from Softwood", Applied Microbiology and Biotechnology, vol. 59, 2002, pp. 618-628.
Ong, "Conversion of Lignocellulosic Biomass to Fuel Ethanol—A Brief Review", The Planter, vol. 80, Issue No. 941, Aug. 2004, pp. 517-524.
Moller, "Cell Wall Saccharification", Outputs from the EPOBIO Project, Nov. 2006, pp. 1-69.
Mosier et al., "Features of Promising Technologies for Pretreatment of Lignocellulosic Biomass", Bioresource Technology, vol. 96, 2005, pp. 673-686.
Holtzapple et al., "The Ammonia Freeze Explosion (AFEX) process—A Practical Lignocellulose Pretreatment", Applied Biochemistry and Biotechnology, vol. 28/29, Issue No. 1, Mar. 1991, pp. 59-74.
Kumar et al., "Methods for Pretreatment of Lignocellulosic Biomass for Efficient Hydrolysis and Biofuel Production", Industrial & Engineering Chemistry Research, vol. 48, Issue No. 8, 2009, pp. 3713-3729.
Lavarack et al., "The Acid Hydrolysis of Sugarcane Bagasse Hemicellulose to Produce Xylose, Arabinose, Glucose and other Products", Biomass & Bioenergy, vol. 23, Issue No. 5, 2002, pp. 367-380.
Yang et al., "One-Step Catalytic Transformation of Carbohydrates and Cellulosic Biomass to 2, 5 Dimethyltetrahydrofuran for Liquid Fuels", Chem Sus Chem, vol. 3, Issue No. 5, May 25, 2010, pp. 597-603.
Lange et al., "Furfural—A Promising Platform for Lignocellulosic Biofuels", Chem Sus Chem, vol. 5, Issue No. 1, Jan. 9, 2012, pp. 150-166.
Nhien et al., "Design and Optimization of Intensified Biorefinery Process for Furfural Production Through a Systematic Procedure", Biochemical Engineering Journal, vol. 116, Apr. 5, 2016, pp. 166-175, XP029805891.
International Search Report and Written Opinion received for PCT Patent Application No. PCT/US2015/044981, dated Nov. 2, 2015, 8 pages.

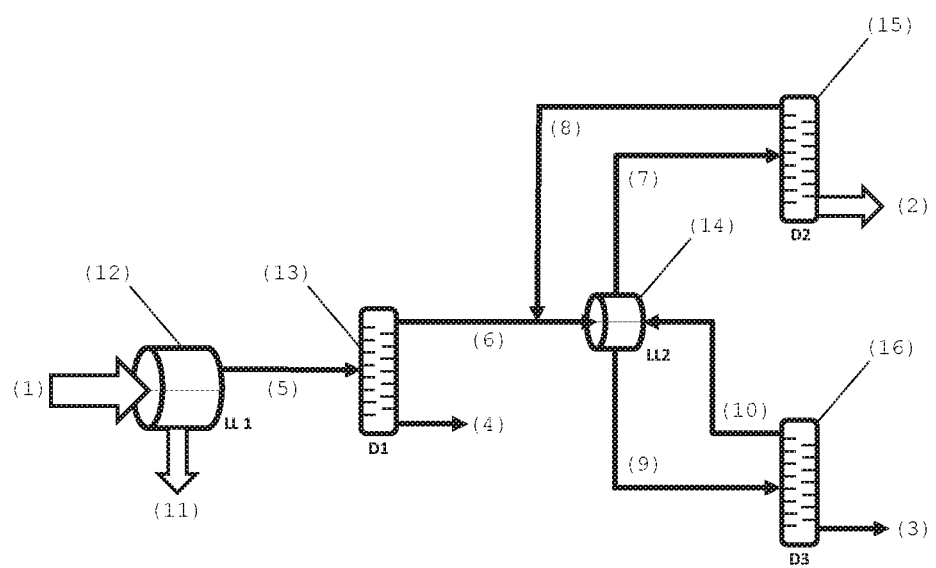

PROCESS FOR THE RECOVERY OF FURFURAL

CROSS REFERENCE TO RELATED APPLICATIONS

This is a national stage application of International Application No. PCT/US2017/058936, filed 30 Oct. 2017, which claims benefit of priority to U.S. Provisional Patent Application No. 62/415,528, filed 1 Nov. 2016.

FIELD OF THE INVENTION

The present invention relates to a process for the high recovery/extraction of furfural from a composition in an energy efficient manner.

BACKGROUND OF THE INVENTION

Furfural is a useful precursor for industrial chemicals, in particular to produce furan and its derivatives.

Furfural may be produced from the hydrolysis of feedstock comprising lignocellulosic biomass. Lignocellulosic biomass comprises mainly hemicelluloses and cellulose, and smaller portions of lignin and protein. Hemicelluloses are a branched polysaccharide of heterogeneous monosaccharide content. Their molecular structure includes the five-carbon monosaccharides ('pentose(s)') xylose and arabinose, as well as the six-carbon monosaccharides ('hexose(s)') mannose, galactose and rhamnose. Due to their xylose and arabinose content, hemicelluloses are a suitable source of monomeric and polymeric pentoses. In comparison, cellulose is a linear-polysaccharide made up of polymerised glucose (a six-carbon monosaccharide/hexose). Compared to cellulose, hemicelluloses are easier to breakdown into their constituent monosaccharides.

Commercially available feedstock comprising lignocellulosic biomass includes bagasse, which is the fibrous matter that remains after sugarcane or sorghum stalks are crushed their juices extracted. An established continuous process for the production of furfural from bagasse is the Rosenlew process, the details of which are discussed in "The Chemistry and Technology of Furfural and its Many By-Products", 1st Edition, K. Zeitsch, pages 48-51 and 303-306.

WO2012041990 describes the production of furfural from bagasse-derived hemicellulose, via its gaseous acid catalysed hydrolysis to pentoses, which are then dehydrated to produce furfural.

WO2016025678 describes the production of furfural, where initially hemicellulose is hydrolysed in a solution comprising α-hydroxysulfonic acid, a portion of the α-hydroxysulfonic acid is then removed from the hydrolysis reaction product to produce an acid-removed stream, and finally the acid-removed stream is subjected to a dehydrating step to produce furfural.

WO2016025679 describes a hydrolysis step, which is buffered to, preferably, less than pH 1, followed by a dehydrating step to produce furfural.

In both WO2016025678 and WO2016025679, during the dehydration reaction step, a "bi-phasic" dehydration reaction mixture is formed by the addition of 'a water-immiscible organic phase' (i.e. a solvent) into the dehydration reaction mixture. The dehydration reaction mixture is then separated into an aqueous product stream, and an organic product stream comprising a portion of furfural. However, WO2016025678 and WO2016025679 do not disclose how furfural can be fully recovered and purified from the organic product stream comprising furfural. Further, WO2016025678 and WO2016025679 do not disclose how furfural remaining in the aqueous product stream can be efficiently recovered and purified from the aqueous product stream.

Solvent extraction of furfural from an aqueous environment is complicated by the carry-over of water into the organic phase, as well as the formation of a furfural-water azeotrope. The extent of the water carry-over depends on the solvent used. Oxygenate solvents, such as those of phenolic compounds, carry more water into the organic phase (approximately around 10,000 ppm to around 40,000 ppm), as compared to aromatic solvents (approximately around 200 ppm to around 1,000 ppm). Further, if furfural is present in an aqueous environment, a furfural-water azeotrope can be formed. It is known in the art of extracting chemical compounds from mixtures of compounds that the presence of any azeotrope increases the energy consumption of a given process, as well as complicating the step and the equipment needed for that process.

Aromatic solvents have a lesser tendency to carry-over water and therefore are less likely to favour the formation of a furfural-water azeotrope, so on the face of it, aromatic solvents seem good candidates for the extraction of furfural. However due to furfural's properties, aromatic solvents' ability to extract furfural is lower than that of oxygenate solvents, which potentially decreases the overall furfural recovery when aromatic solvents are used.

Processes for the production of furfural from biomass lead to the formation of humins and tar, which can adversely interfere with the extraction and purification of furfural. Humins are dark, amorphous and undesirable acid by-products and resinous material resulting from sugars, and other organic compound degradation. Tar is a generic reference to organic material which is insoluble in water, which is dark in colour, and which tends to become viscous and very dark to almost black when concentrated. Particularly, the separation of an organic phase from an aqueous phase, and/or the later separation or purification steps can be adversely affected.

The inventors of the present invention have observed that such problems due to the formation of humins and tar are applicable in the formation, and during the extraction and purification of furfural from lignocellulosic biomass, but may be alleviated by the use of oxygenate solvents, rather than aromatic solvents.

Regarding energy consumption, the Rosenlew process uses azeotropic distillation to isolate furfural from the reaction mix by, and does not use solvent extraction. The Rosenlew process consumes about 10 tonnes of steam to recover each tonne of furfural.

It would, therefore, be advantageous to provide a process for the recovery of furfural that is more energy-efficient, which provides a high-yield of furfural than the prior art processes, as well as one which does not suffer from the interference of humins and tar.

SUMMARY OF THE INVENTION

Accordingly, the present invention provides a process for the extraction of furfural from a composition comprising furfural, water, at least one inorganic acid, at least one organic acid and an oxygenate solvent with a boiling point higher than that of furfural; said process comprising:
(a) subjecting the composition to a first liquid-liquid separation step to provide: (i) an organic phase comprising the oxygenate solvent, furfural and a portion of the at least one organic acid, and (ii) an aqueous phase comprising the at least one inorganic acid and the remainder of the at least one organic acid;

(b) subjecting the organic phase of step (a) to a first distillation step to provide: (i) a first top stream comprising furfural, and a portion of at least one organic acid, and (ii) a first bottom stream comprising the oxygenate solvent;

(c) subjecting the first top stream of step (b) to a second liquid-liquid separation step to provide: (i) a second top stream comprising a portion of the furfural and a portion of at least one organic acid, and (ii) a second bottom stream comprising a portion of the furfural and a portion of the at least one organic acid; and (d) subjecting the second top stream of step (c) to a second distillation step to provide: (i) a third top stream comprising a furfural-water azeotrope, and (ii) a third bottom stream comprising furfural.

The composition may derived from a product stream of a pentose dehydration step wherein a pentose feed stream is dehydrated.

The pentose feed stream may be derived from the hydrolysis of a lignocellulosic biomass.

The oxygenate solvent is selected from the group consisting of: propyl guaiacol; propyl syringol; guaiacyl propanol; syringyl propanol; nonyl phenol; o-, m-, p-substituted cresols; guaiacol; 2-methoxy-4-propylphenol; eugenol; sec-butyl phenol; 2,6-xylenol; 2,5-xylenol; and any combination thereof.

A portion of the first bottom stream of step (b) comprising the oxygenate solvent may be recycled into the first liquid-liquid separation step.

A portion of the third top stream from step (d) comprising the furfural-water azeotrope may be recycled back to feed either the first distillation step or the first liquid-liquid separator.

The second bottom stream of step (c) comprising a portion of the furfural and a portion of the at least one organic acid may be recycled back to feed the first liquid-liquid separator.

The second bottom stream of step (c) comprising a portion of the furfural and a portion of the at least one organic acid may be subjected to a third distillation step to provide: (i) a fourth top stream comprising a portion of the furfural, and (ii) a fourth bottom stream comprising water and the at least one organic acid.

BRIEF DESCRIPTION OF THE DRAWING

FIG. 1 shows a simplified schematic diagram of an embodiment of the process according to the invention.

DETAILED DESCRIPTION OF THE INVENTION

The present inventors have surprisingly found that the process for the extraction of furfural according to the present invention provides a higher yield of furfural than known processes, and consumes less energy to produce each tonne of furfural, suitably, by consuming less than 6 tonnes of steam to recover each tonne furfural with a furfural recovery of around 99%.

In the process according to the present invention, furfural is extracted from a composition comprising furfural, water, at least one organic acid and an oxygenate solvent with a boiling point higher than that of furfural.

In an embodiment of the present invention the composition may be derived from a product stream of a pentose dehydration step, wherein a pentose feed stream is dehydrated.

Suitably, the pentose dehydration step dehydrates a pentose feed stream comprising monomeric and polymeric pentoses, which is derived from a hydrolysis step wherein a lignocellulosic biomass is hydrolysed in the presence of at least one inorganic acid; although as an alternative, other processes may also be used to hydrolyse the lignocellulosic biomass, such as ones which may use basic or neutral pH conditions. Suitably, the lignocellulosic biomass hydrolysis step is as described in WO2016025678 and WO2016025679.

Where used for the hydrolysis of lignocellulosic biomass, suitably, the at least one inorganic acid may be selected from, such as but not limited to, hydrochloric acid, nitric acid, phosphoric acid, boric acid sulphuric acid and α-hydroxysulfonic acid, or combinations thereof.

Suitably, some types of lignocellulosic biomass may intrinsically contain at least one organic acid, or will form at least one organic acid upon being subjected to the hydrolysis. Examples of such acids include, but are not limited to, formic acid, acetic acid, lactic acid, glycolic acid, levulinic acid, oxalic acid and citric acid, or combinations thereof. When using such types of biomass material, the need to add at least one acid inorganic acid may be reduced or even eliminated as the in-situ generated acid may provide the necessary acidic pH.

According to an embodiment of the invention, the composition may be derived from the product stream of a pentose dehydration step; said product stream is also hereinafter referred to as the "dehydration product stream".

Suitably, the pentose dehydration step takes place in a dehydration reaction mixture, where the dehydration of monomeric and polymeric pentoses is catalysed by at least one inorganic acid at an elevated temperature, although at least one organic acid may also take part in such catalysis.

The dehydration reaction mixture comprises the pentose feed stream, at least one inorganic acid, at least one organic acid and furfural; the level of the furfural depending on how long the pentose dehydration step has been running.

The at least one inorganic acid and the at least one organic acid present in the dehydration reaction mixture will have carried through in the pentose feed stream from the hydrolysis step to the pentose dehydration step, where the hydrolysis step precedes the pentose dehydration step. However, if the hydrolysis step was carried out under basic or neutral pH conditions as an alternative, or if it is determined that the pH of the dehydration reaction mixture is not acidic enough, more inorganic acid may be added to the dehydration reaction mixture.

Preferably, the pentose dehydration step is carried out at the elevated temperature of at least 100° C., more preferably at least 110° C., and even more preferably at least 140° C. Preferably, the pentose dehydration step is carried out at the elevated temperature of at most 250° C., more preferably at most 200° C., and even more preferably at most 150° C.

Preferably, the pentose dehydration step is carried out for a period of at least 1 second, more preferably at least 5 minutes, even more preferably at least 10 minutes and most preferably at least 30 minutes. Preferably, the pentose dehydration step is carried out for a period of at most 24 hours, more preferably at most 12 hours, even more preferably at most 5 hours and most preferably at most 2 hours.

One or more oxygenate solvents may be added to the dehydration reaction mixture. The presence of the oxygenate solvent in the dehydration reaction mixture creates an aqueous phase and an organic phase.

Preferably, the dehydration reaction mixture to oxygenate solvent ratio is at least 1 to 0.05% vol., more preferably said ratio is 1 to 0.1% vol., even more preferably said ratio is 1 to 0.25% vol., most preferably said ratio is 1 to 0.4% vol.

Preferably, the dehydration reaction mixture to oxygenate solvent ratio is at most 1 to 2.5% vol., more preferably said ratio is 1 to 1.25% vol., even more preferably said ratio is 1 to 0.75% vol., most preferably said ratio is 1 to 0.6% vol.

Preferably, the oxygenate solvent is selected from the group consisting of, but not limited to, propyl guaiacol, propyl syringol, guaiacyl propanol, syringyl propanol, nonyl phenol, o-, m-, p-substituted cresols, guaiacol, 2-methoxy-4-propylphenol, eugenol, sec-butyl phenol, 2,6-xylenol, 2,5-xylenol. Optionally, tetrahydrofuranic compounds may also be selected.

Suitably, the oxygenate solvent may be a mixture of any combination of the afore-mentioned solvents.

The oxygenate solvent may be added to the dehydration reaction mixture at the start of, or part way through, the pentose dehydration step.

Suitably, the oxygenate solvent may also be added to the dehydration product stream to form the composition, if the pentose dehydration step did not occur in the presence of the oxygenate solvent.

However, preferably, the oxygenate solvent may be added to the dehydration reaction mixture at the start of the pentose dehydration step. Optionally, the source of the oxygenate solvent may be a recycle stream from one or more of steps of the process of the present invention, such stream being recycled as a feed to the pentose dehydration step.

If the oxygenate solvent is added to the dehydration reaction mixture at the start of, or part way through, the pentose dehydration step, the formation of furfural mainly takes place in the aqueous phase. Therefore the amount of furfural in the organic phase varies depending on how far the pentose dehydration step has progressed.

Suitably, the oxygenate solvent has selectivity towards furfural over water and over the at least one inorganic acid, and selectively extracts furfural from said aqueous phase into the organic phase as the pentose dehydration step converts the pentose feed stream into furfural.

The oxygenate solvent also has selectivity towards furfural over the at least one organic acid, however depending on the oxygenate solvent, around 10,000 ppm to around 40,000 ppm water may partition into the organic phase, leading to a significant amount of at least one organic acid partitioning into the into the organic phase, which needs to be separated from the furfural.

Suitably, the oxygenate solvent provides at least three advantages. Firstly, compared to, for example, aromatic solvents, the oxygenate solvent carries-over more water into the organic phase, and it suitably extracts more furfural from the dehydration reaction mixture, leaving an insignificant amount of furfural in the aqueous phase. This in turn means that only an organic phase has to be processed to recover furfural.

Secondly, compared to, for example, aromatic solvents, the use of oxygenate solvent alleviates in the pentose dehydration step the problems caused due to humins and tar, and in the subsequent processing step, including in the process of the present invention.

Thirdly, because the boiling point of water at ambient pressure is lower than the boiling point of furfural at ambient pressure (about 100° C. versus about 161° C., respectively) extraction of the furfural from the dehydration reaction product stream reduces the need to boil-off significant amount of water to purify the furfural from water. Instead, because the oxygenate solvent has a boiling point higher than that of furfural, furfural can be distilled off from the oxygenate solvent, and since the quantity of furfural in the oxygenate solvent is only a fraction per unit volume of the oxygenate solvent, in processes such as distillation, a lesser quantity of material (i.e. the furfural with its lower boiling point) needs to be boiled off. Suitably, this provides an energy advantage (saving).

However, due to the extent of water carry-over into the organic phase of an oxygenate solvent, not only furfural in the organic phase tends to form a furfural-water azeotrope, but also at least one organic acid may partition into the organic phase. These issues may, on the face of it, appear to complicate the recovery of furfural and make it more energy demanding. However, as only an organic phase has to be processed to recover furfural, any increase in energy cost of processing furfural-water azeotrope, and the removal of an at least one organic acid, is offset by not needing to process an aqueous phase, as processing the latter involves boiling off large quantities of water.

FIG. 1 shows a simplified schematic diagram of an embodiment of process according to the invention.

In the process according to the present invention, furfural is extracted from a composition (1) comprising furfural, water, at least one organic acid, and an oxygenate solvent with a boiling point higher than that of furfural.

To commence the extraction of furfural from the composition, the composition (1) is subjected to a first liquid-liquid separation step in a first liquid-liquid separator (12) to provide: (i) an organic phase (5) comprising the oxygenate solvent, furfural and a portion of the at least one organic acid, and (ii) an aqueous phase (11) comprising the remainder of the at least one organic acid.

Preferably, the first liquid-liquid separation may be operated at a temperature of at most 200° C., more preferably at a temperature of at most 180° C., even more preferably at a temperature of at most 160° C., even more preferably at a temperature of at most 150° C., so long as the liquid separates into two phases at the separation temperature.

Preferably, the first liquid-liquid separation may be operated at a temperature of at least ambient temperature, more preferably at a temperature of at least 60° C., even more preferably at a temperature of at least 100° C., even more preferably at a temperature of at least 130° C., so long as the liquid separates into two phases at the separation temperature.

The first liquid-liquid separation step is carried out in any suitable liquid-liquid separator as would be known to the person skilled in the art.

Prior to undergoing the first liquid-liquid separation step, the composition may optionally be routed through a, preferably solid/liquid, separation step, to remove any insoluble humins or other tar that may have been formed during the dehydration step.

In the process of the present invention the organic phase from the first liquid-liquid separation step is subjected to a first distillation step (13) to provide: (i) a first top stream (6) comprising furfural, and a portion of the at least one organic acid, and (ii) a first bottom stream (4) comprising the oxygenate solvent.

Furfural has a boiling point at ambient pressure of about 161° C. and the furfural-water azeotrope has a boiling point at ambient pressure of about 98° C., and as the oxygenate solvent has a boiling point higher than that of furfural, a first top stream comprising furfural is obtained. Suitably, the greater the difference between the boiling point of furfural and the oxygenate solvent, the easier and cleaner the separation between these compounds will be.

Suitably the oxygenate solvent may be sec-butyl phenol, which has a boiling point of around 240° C. at ambient pressure, and suitably this gives sufficient difference in respective boiling points to achieve good furfural separation.

Suitably, although the oxygenate solvent has a preferred selectivity towards furfural, not only a furfural-water azeotrope, but also at least one organic acid may be present in the aqueous phase of the composition.

These complicate the recovery of furfural from the composition as the boiling point of the furfural-water azeotrope at ambient pressure is about 98° C., this being very close to the boiling point of water from which it needs to be separated from. Further the at least one organic acid also needs to be separated from the furfural, while maintaining energy efficiency.

Following the first liquid-liquid separation step, in order to achieve both high furfural recovery and high furfural purity, furfural needs to be recovered efficiently from the organic phase.

Therefore, to achieve this, the inventors of the present invention have introduced a second liquid-liquid separation step (14) into the process of the present invention, which takes advantage the property of the furfural-water azeotrope to phase separate under certain temperatures.

The inventors of the present invention have also introduced a process loop that not only separates furfural from the furfural-water azeotrope, but also optionally recycles any remaining furfural-water azeotrope back as a feed to the first distillation step (13) or the first liquid-liquid separator (12).

Therefore in the process of the present invention, the first top stream (6) from the first distillation step is subjected to a second liquid-liquid separation step (14) to provide: (i) a second top stream (7) comprising a portion of the furfural and a portion of at least one organic acid, and (ii) a second bottom stream (9) comprising a portion of the furfural and a portion of the at least one organic acid.

Preferably, the second liquid-liquid separation may be operated at a temperature of at most 120° C., more preferably at a temperature of at most 100° C., even more preferably at a temperature of at most 80° C., even more preferably at a temperature of at most 60° C., so long as the liquid separates into two phases at the separation temperature.

Preferably, the second liquid-liquid separation may be operated at a temperature of at least ambient temperature, more preferably at a temperature of at least 30° C., even more preferably at a temperature of at least 40° C., even more preferably at a temperature of at least 50° C., so long as the liquid separates into two phases at the separation temperature.

In the process of the present invention, following the second liquid-liquid separation step (14), the second top stream from the second liquid-liquid separation step is subjected to a second distillation step (15) to provide: (i) a third top stream (8) comprising a furfural-water azeotrope; and (ii) a third bottom stream (2) comprising furfural.

To achieve energy efficiency through not having to heat up new material which is to be introduced to the process, as well as to increase the utility of the oxygenate solvent, the process of the present invention can optionally recycle the oxygenate solvent. To do this, suitably a portion of the first bottom stream from the first distillation step comprising the oxygenate solvent is recycled into the first liquid-liquid separation step, and optionally to the pentose dehydration step.

Optionally in the process of the present invention, a portion of the third top stream (8) from the second distillation step comprising the furfural-water azeotrope is recycled back to feed either the first liquid-liquid separator (12) in one embodiment, or the first distillation step (13) in another embodiment.

Optionally in the process of the present invention, the second bottom stream (9) from the second liquid-liquid separator comprising a portion of the furfural and a portion of the at least one organic acid is recycled back to feed the first liquid-liquid separator (12).

Optionally in the process of the present invention, the second bottom stream (9) from the second liquid-liquid step comprising a portion of the furfural and a portion of the at least one organic acid is subjected to a third distillation step (16) to provide: (i) a fourth top stream (10) comprising a portion of the furfural, and (ii) a fourth bottom stream (3) comprising water and the at least one organic acid.

Optionally, each of the first distillation step, the second distillation step and the third distillation step may be either atmospheric distillation, and vacuum distillation, where if the latter the vacuum column may be operated at a pressure down to around 0.00133 MPa (10 mmHg).

EXAMPLE

A process line up as depicted in FIG. 1 was assessed for furfural recovery using process modelling Aspen plus (Version 7.3) software licensed from Aspen Technology Inc., MA.

The modelled process line up is representative of a furfural separation scheme from a process stream containing furfural on a furfural manufacturing plant.

The results obtained in this example are representative of expected furfural recovery rates, fraction of furfural recovery from feed stream, furfural purity, heat duty (MW), and steam usage measured in tonne of steam/tonne of furfural produced.

Thermodynamic data contained in 'NRTL-HOC property method' set was used in this simulation.

Steam consumption in the process line up was determined on the basis of using 4.48 MPa high pressure steam.

The feed stream (1) contains water, furfural, acetic acid (as at least one organic acid), Sec-butyl phenol (SBP) (representative of an oxygenate solvent with a boiling point higher than that of furfural).

Separation scheme enables separation of furfural from the composition with high purity and allows for recycle of solvent for re-use in the process.

Table 1 present all the process stream data output.

Table 2 and 3 give process operating conditions and results summary for distillation columns and liquid-liquid separators used in the process line-up.

Table 4 presents the summary of results for furfural separation scheme.

Based on the simulation output this separation process line up consumes about 5.6 tonne steam/tonne furfural produced. This is about 44% reduction in steam usage compared to consumption of 10 tonne steam/tonne furfural produced in the state-of-the-art Rosenlew's process for commercial furfural production

TABLE 1

Stream Summary Results

| Component | Stream # | | | | | | | | | | |
|---|---|---|---|---|---|---|---|---|---|---|---|
| Mass Flow | 7 | 9 | 10 | 3 | 6 | 4 | 8 | 2 | 1 | 5 | 11 |
| Water (tonnes/day) | 75 | 421 | 134 | 287 | 287 | 0 | 75 | 0 | 14365 | 287 | 14078 |
| Furfural (tonnes/day) | 670 | 65 | 65 | 0 | 625 | 0 | 46 | 624 | 631 | 625 | 6 |
| Acetic Acid (tonnes/day) | 31 | 24 | 1 | 23 | 25 | 0 | 29 | 2 | 240 | 25 | 215 |
| SBP (tonnes/day) | 0 | 0 | 0 | 0 | 0 | 7182 | 0 | 0 | 7182 | 7182 | 0 |
| Mass Flow | 777 | 510 | 200 | 310 | 937 | 7182 | 150 | 627 | 22418 | 8119 | 14299 |
| Temperature (° C.) | 90 | 90 | 97 | 100 | 98 | 240 | 99 | 161 | 90 | 90 | 90 |

TABLE 2

Distillation Column Summary

| | Units | D1 | D2 | D3 |
|---|---|---|---|---|
| Pressure | MPa | 0.1 | 0.1 | 0.1 |
| Reflux Ratio | | 1 | 1 | 1 |
| Distillate Rate | tonne/day | 936.5 | 150 | 200 |
| Number of trays | | 25 | 25 | 25 |
| Feed rate | tonne/day | 8119 | 777 | 510 |
| Reboiler Temperature | ° C. | 240 | 161 | 100 |
| Reboiler Duty | MW | 55 | 5 | 8 |
| Steam usage (4.48 MPa) | tonne/day | 2818 | 276 | 399 |

TABLE 3

Liquid-Liquid Separator Summary

| | Units | LL1 | LL2 |
|---|---|---|---|
| Pressure | MPa | 0.1 | 0.1 |
| Temperature | ° C. | 90 | 90 |
| Feed rate | tonne/day | 22418 | 1287 |

TABLE 4

Separation Scheme Results Summary

| | Units | |
|---|---|---|
| Furfural Recovery Rate | tonne/day | 624.5 |
| Furfural Recovery | | 99.0% |
| Furfural Purity | | 99.6% |
| Total energy requirement | MW | 68 |
| Steam Usage (650 psig) | tonne/day | 3493 |
| Steam Consumption | t/t FUR produced | 5.6 |

That which is claimed is:

1. A process for the extraction of furfural from a composition comprising furfural, water, at least one organic acid and an oxygenate solvent with a boiling point higher than that of furfural, said process comprising:
   (a) subjecting the composition to a first liquid-liquid separation step to provide:
      an organic phase comprising the oxygenate solvent, furfural, and a portion of the at least one organic acid; and
      an aqueous phase comprising the remainder of the at least one organic acid;
   (b) subjecting the organic phase of step (a) to a first distillation step to provide:
      a first top stream comprising furfural, and a portion of at least one organic acid; and
      a first bottom stream comprising the oxygenate solvent;
   (c) subjecting the first top stream of step (b) to a second liquid-liquid separation step to provide:
      a second top stream comprising a portion of the furfural and a portion of at least one organic acid; and
      a second bottom stream comprising a portion of the furfural and a portion of the at least one organic acid;
   (d) subjecting the second top stream of step (c) to a second distillation step to provide:
      a third top stream comprising a furfural-water azeotrope; and
      a third bottom stream comprising furfural; and
   (e) subjecting the second bottom stream to a third distillation step to provide:
      a fourth top stream comprising a portion of the furfural which is recycled back to feed the second liquid-liquid separation step, and
      a fourth bottom stream comprising water and the at least one organic acid.

2. The process according to claim 1, wherein the composition is derived from a product stream of a pentose dehydration step wherein a pentose feed stream is dehydrated.

3. The process according to claim 2, wherein the pentose feed stream is derived from the hydrolysis of a lignocellulosic biomass.

4. The process according to claim 1, wherein the oxygenate solvent is selected from the group consisting of: propyl guaiacol; propyl syringol; guaiacyl propanol, syringyl propanol; nonyl phenol; o-, m-, p-substituted cresols; guaiacol; 2-methoxy-4-propylphenol; eugenol; 2,6-xylenol; sec-butyl phenol; 2,5-xylenol; and any combination thereof.

5. The process according to claim 1, wherein a portion of the first bottom stream of step (b) comprising the oxygenate solvent is recycled into the first liquid-liquid separation step.

6. The process according to claim 1, wherein a portion of the third top stream from step (d) comprising the furfural-water azeotrope is recycled back to feed either the first distillation step or the first liquid-liquid separator.

7. The process according to claim 1, wherein the second bottom stream of step (c) comprising a portion of the furfural and a portion of the at least one organic acid is recycled back to feed the first liquid-liquid separator.

* * * * *